United States Patent
Schulzetenberg et al.

(10) Patent No.: US 11,888,325 B2
(45) Date of Patent: Jan. 30, 2024

(54) IMPLANTABLE MEDICAL SYSTEM WITH EXTERNAL POWER CHARGER

(71) Applicant: MEDTRONIC, INC., Minneapolis, MN (US)

(72) Inventors: Robert M. Schulzetenberg, Columbia Heights, MN (US); Venkat R. Gaddam, Plymouth, MN (US); Jason H. Harper, Vadnais Heights, MN (US); Brett Otteson, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 457 days.

(21) Appl. No.: 17/124,663

(22) Filed: Dec. 17, 2020

(65) Prior Publication Data

US 2021/0194289 A1    Jun. 24, 2021

Related U.S. Application Data

(60) Provisional application No. 62/949,747, filed on Dec. 18, 2019.

(51) Int. Cl.
*H02J 50/12* (2016.01)
*H02J 50/80* (2016.01)
(Continued)

(52) U.S. Cl.
CPC ............ *H02J 50/12* (2016.02); *A61B 5/0015* (2013.01); *A61B 5/0031* (2013.01);
(Continued)

(58) Field of Classification Search
CPC .......... H02J 50/12; H02J 7/00032; H02J 7/02; H02J 50/50; H02J 50/80; A61B 5/0015;
(Continued)

(56) References Cited

U.S. PATENT DOCUMENTS 9,259,591 B2    2/2016 Brown et al.
9,821,112 B2 *  11/2017 Olson ..................... H02J 50/70
(Continued)

FOREIGN PATENT DOCUMENTS

EP      3131623 B1      6/2018
WO      2011119352 A1   9/2011

OTHER PUBLICATIONS (PCT/US2020/065920) PCT Notification of Transmittal of the International Search Report and the Written Opinion of the International Searching Authority, dated Mar. 25, 2021, 9 pages.

*Primary Examiner* — Jared Fureman
*Assistant Examiner* — Michael J Warmflash
(74) *Attorney, Agent, or Firm* — Shumaker & Sieffert, P.A.

(57) ABSTRACT

An implantable medical system includes an implantable medical device and a external charger. The implantable medical device includes a rechargeable power source, electronic components coupled to the rechargeable power source to deliver a therapy to or monitor a parameter of a patient, and a recharge system operably coupled to the rechargeable power source including a secondary coil to receive power via an inductive power transfer. The external charger includes a housing forming an internal compartment, recharger electronic components disposed on a printed circuit board assembly in the internal compartment, and a recharge coil assembly disposed within the internal compartment, the recharge coil assembly including a recharge coil to provide power to the secondary coil via the inductive power transfer and a flux guide having a ferrite sheet disposed between the recharge coil and the printed circuit board assembly.

46 Claims, 5 Drawing Sheets

(51) Int. Cl.

| | | |
|---|---|---|
| *H02J 50/50* | (2016.01) | |
| *H02J 7/00* | (2006.01) | |
| *A61B 5/00* | (2006.01) | |
| *A61N 1/05* | (2006.01) | |
| *A61N 1/372* | (2006.01) | |
| *A61N 1/378* | (2006.01) | |
| *H02J 7/02* | (2016.01) | |
| *H04B 5/00* | (2006.01) | |

(52) U.S. Cl.
CPC ......... *A61N 1/0551* (2013.01); *A61N 1/3787* (2013.01); *A61N 1/37235* (2013.01); *H02J 7/00032* (2020.01); *H02J 7/02* (2013.01); *H02J 50/50* (2016.02); *H02J 50/80* (2016.02); *H04B 5/0037* (2013.01); *H04B 5/0075* (2013.01)

(58) Field of Classification Search
CPC ............... A61B 5/0031; A61N 1/0551; A61N 1/37235; A61N 1/3787; A61N 1/37223; H04B 5/0037; H04B 5/0075
See application file for complete search history.

(56) References Cited

U.S. PATENT DOCUMENTS

| | | | |
|---|---|---|---|
| 10,971,950 B2* | 4/2021 | Dearden | H02J 50/10 |
| 2005/0288743 A1* | 12/2005 | Ahn | A61N 1/3787 |
| | | | 607/61 |
| 2015/0290379 A1* | 10/2015 | Rudser | A61N 1/3787 |
| | | | 600/16 |
| 2018/0036477 A1* | 2/2018 | Olson | A61N 1/3655 |
| 2018/0140851 A1 | 5/2018 | Maile et al. | |

* cited by examiner

IMPLANTABLE MEDICAL SYSTEM WITH EXTERNAL POWER CHARGER

CROSS-REFERENCE TO RELATED APPLICATION

This Non-Provisional Utility application claims benefit to U.S. Provisional Application No. 62/949,747, filed Dec. 18, 2019, titled "EXTERNAL POWER CHARGER," the entirety of which incorporated herein by reference.

BACKGROUND

The present disclosure relates generally to medical devices. More particularly, the present disclosure relates to devices that charge and may communicate with implantable medical devices.

Wireless power transfer or transmission is used to deliver power from a power source without a mechanical connection to electronic devices. Wireless power transfer systems are used in a variety of applications, such as, for recharging batteries in mobile computing devices such as smart phones or wearable devices. Wireless power transfer systems are also used to transmit power transcutaneously, or through the skin, to medical devices implanted in a patient either to directly power the implanted medical device or to recharge an energy storage system of the implanted medical device. The implantable medical device may be implanted within a patient and perform a task such as to monitor a parameter of the patient or to deliver a therapy to the patient. In one example, the implantable medical device is an implantable neurostimulator implanted into the patient and used to provide nerve stimulation via an electrical lead. Many implantable medical devices are designed to receive power directly from an energy storage system such as a battery or capacitor located with the implantable medical device, but the energy storage system often becomes depleted of energy long before the end of the useful life of the implantable medical device. The implantable medical device may include a rechargeable energy storage system such as a rechargeable battery to extend the life of the implantable medical device. A wireless charger may be applied to recharge a depleted battery in the implanted medical device. From time to time, the wireless charger and the implanted medical device may also wirelessly and transcutaneously exchange communication signals.

In some examples, transcutaneous charging is performed via inductive power transfer or transmission. The energy storage system of the implantable medical device can be recharged with an external charger configured to provide inductive power transfer. Inductive power transfer can be performed with an inductive coupling between coils of wire such as a primary coil in the charger and a secondary coil in the implantable medical device. Power is transferred between the coils with a magnetic field. An alternating current (AC) through the primary coil creates an oscillating magnetic field. The magnetic field passes through the secondary coil, and the magnetic field induces an alternating electromotive force, or EMF, (voltage), which creates an alternating current in the secondary coil. The induced alternating current may either directly drive a load in the implantable medical device, or be rectified to direct current (DC) by a rectifier in the implantable medical device, which drives the load. Resonant inductive coupling is a type of inductive coupling in which power is transferred by magnetic fields between two resonant circuits, one in the charger and one in the implantable medical device. Each resonant circuit includes a coil of wire connected to a capacitor, or a self-resonant coil or other resonator with internal capacitance. Resonant circuits, or tank circuits, are tuned to resonate at generally the same resonant frequency. The resonance between the coils can greatly increase coupling and power transfer between the charger and the implantable medical device. In this example, the external charger does not mechanically connect with the implantable medical device, and the external charger can be used to charge the implantable medical device from a relatively short distance away.

SUMMARY

Current wireless power chargers may include multiple internal compartments to separate the primary coil from the electronic components and battery. For example, U.S. Pat. No. 9,821,112 to Olson et al. (which is incorporated by reference into this disclosure) describes an example of an external charger having an external antenna with a primary coil separate from a charging unit having electronics and battery to drive the primary coil. Additional components are used in the charger to separate the primary coil from the electronic components and battery, which increases costs and creates a more cumbersome wireless power charger. Simply combining all the elements into a single compartment, however, can create undesirable effects such as loading to the primary coil from conductive elements of printed circuit boards, such as a ground plane, that generates a reflected impedance on the primary coil. For instance, the introduction of a ground plane in proximity with a primary coil may increase the resistance by a factor of ten leading to significant inefficiencies in power transfer that can increase the length of a recharge session and cause excessive heating of the primary recharger.

A disclosed external charger includes a primary coil within the same internal compartment as the electronics and battery. In one example, the charger includes a housing that defines an internal compartment that includes printed circuit board assemblies, a battery, and a recharge coil assembly. The recharge coil assembly can operate as a primary coil to deliver magnetic energy to recharge an energy storage system on an implantable medical device with a corresponding secondary coil. The recharge coil assembly in the example includes a flat, coreless recharge coil on a plastic or insulative bobbin with a flux guide such as a ferrite sheet disposed between the recharge coil and the printed circuit board assemblies. The recharge coil assembly also includes a flat telemetry coil that is concentric and coplanar with the recharge coil and spaced-apart from the recharge coil. In one example, the telemetry coil is wound on the plastic bobbin around the outer diameter of the recharge coil. The telemetry coil can exchange communication with the implanted medical device via inductive telemetry using an inductive telemetry protocol such as Telemetry N. The flux guide can include a ferrite sheet that is configured to reduce loading to the recharge coil assembly from the printed circuit board assemblies and to amplify magnetic flux towards the implantable medical device during a recharge session.

In addition to inductive recharge, the charger can provide for multiple telemetry schemes from the components in the internal compartment. For example, the telemetry schemes can include a near-field inductive telemetry such as Telemetry N, a distance or radiofrequency telemetry such as Telemetry M, and Bluetooth Low Energy for communication with external computing devices such as a smart phone. The radiofrequency telemetry antenna can be placed within the internal compartment.

In addition to the flux guide, the printed circuit board assemblies can be configured and stacked to reduce reflected impedance on the recharge coil assembly. Relays can be applied to the recharge coil and the inductive telemetry coil to decouple the respective tank circuits when inactive to eliminate magnetic coupling between the coils.

DETAILED DESCRIPTION

Aspects of the present disclosure provide for an external charger for implantable medical devices, methods of manufacturing such external charger, and implantable medical device systems including such external charger.

Figure 1:
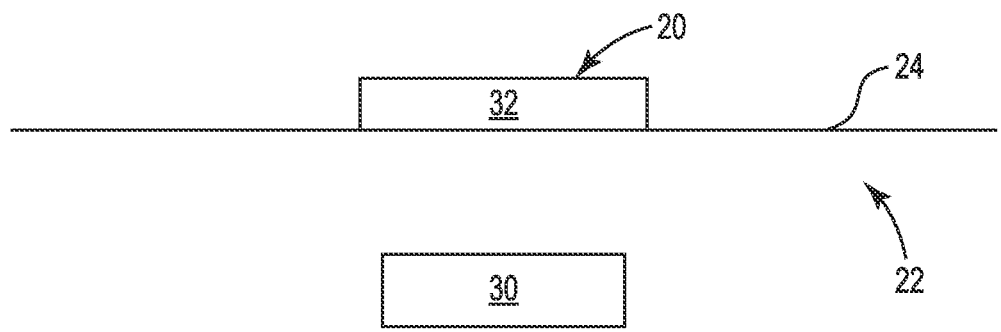
FIG. 1 is a schematic diagram illustrating an example implantable medical system including an implantable medical device and an external charger of the present disclosure.

FIG. 1 illustrates an implantable medical device system 20. System 20 includes an implantable medical device 30, which can be fully implanted within a patient 22. The implantable medical device 30 can include an energy storage system, such as a rechargeable battery, and circuitry within the implantable medical device 30 to apply energy from the battery. The system 20 also includes a charger 32, which can colloquially be referred to as a wireless recharger, outside of the patient 22, or across transcutaneous boundary 24 such as the surface of the patient's skin proximate the implantable medical device 30. In one example, the charger 32 is placed against the patient 22 and proximate the implantable medical device 30 to inductively transfer energy and to replenish the battery of the implantable medical device 30. The charger 32 can include a primary coil to inductively couple with a secondary coil in the implantable medical device 30 and provide an inductive power transfer to recharge the battery when placed proximate the implantable medical device 30.

Systems of the present disclosure can optionally include addition components. For example, system 20 can also optionally include a handset programmer configured to wirelessly interface with the implantable medical device 30 or with the charger 32. In one example, the handset programmer can be implemented as a software application hosted on a general-purpose computing device or mobile computing device. System 20 can include a charging dock, which can be plugged into a wall outlet and configured to charge an internal battery of the charger 32. The charger 32 can also be used in conjunction with a fixation product of system 20 to keep the charger 32 in position proximate the implantable medical device 30 during a recharge session. The fixation product can include a fixation belt to be worn around a portion of the patient 22 such as the belt line for implantable medical device 30 in the abdomen, buttocks or flank of the patient 22, or a fixation drape to be worn around the neck with a counterweight to balance the charger 32 for an implantable medical device 30 in the pectoral region of the patient 22. The fixation product receives the charger 32 to hold the charger 30 in place with respect to the fixation product so that the charger 32, in one example, does not rotate and generally does not move with respect to the implantable medical device 30 during the recharge session and to secure the charger 32 so as not to fall out unless purposefully removed from the fixation product The implantable medical device 30 may be of various types, such as a device for producing electrical stimulation or for sensing physiological signals for various medical applications such as neurological or cardiac therapy. An example of such an implantable pulse generator is available under the trade designation Medtronic InterStim Neurostimulator from Medtronic, Inc. In one example, the implantable medical device 30 can be configured to provide a small form factor, e.g., a volume on the order of approximately three cubic centimeters in some examples, and generate desired stimulation signals over an extended lifetime. The implantable medical device 30 can be described as an implantable neurostimulator for illustration. For example, the implantable medical device 30 is configured to be useful or appropriate for providing stimulation therapy to the patient 22, and in particular sacral neuromodulation. The implantable medical device 30 can serve as the power source of the sacral neuromodulation therapy. In such examples, the implantable medical device 30 delivers electrical stimulation to the sacral nerve.

Sacral neuromodulation therapy can be indicated for the management of the chronic intractable functional disorders of the pelvis and lower urinary or intestinal tract including overactive bladder, fecal incontinence, and nonobstructive urinary retention. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles within the sacrum. The sacrum, generally, is a large, triangular bone situated at the lower part of the vertebral column, and at the upper and back part of the pelvic cavity. The spinal canal runs throughout the greater part of the sacrum. The sacrum is perforated by the anterior and posterior sacral foramina that the sacral nerves pass through.

Sacral neuromodulation creates an electrical field near the sacral nerve to modulate the neural activity that influences the behavior of the pelvic floor, lower urinary tract, urinary and anal sphincters, and colon. The implantable medical device 30 is configured to use current controlled stimulation to generate an electric field to modulate the sacral nerve. Electrical stimulation is delivered using metal electrodes provided with an implantable medical lead (not shown) coupled to implantable medical device 30. The implantable medical lead includes a proximal end of a lead body in which a series of electrical contacts are located. Each electrical contact has a corresponding conductor within the lead body that extends to a distal end where a series of electrodes are present. During use, the proximal end is inserted into the implantable medical device, establishing an electrical interface between the electrical contacts of the implantable medical lead and electrical connectors carried by the implantable medical device 30. The implantable medical device 30 generates stimulation signals that are delivered to the distal end of the implantable medical lead and to targeted tissue, or signals sensed by the distal end of the implantable medical lead at the targeted tissue are delivered to the implantable medical device 30.

The implantable medical lead includes an electrode and is configured to carry current in the form of electrons, to biological tissue, which carries current in the form of ions. An interface between the electrode and the tissue includes non-linear impedance that can be a function of the voltage across that interface. During current-controlled stimulation, an amount of current is regulated. The voltage is changed according to the actual value of impedance, such that changes in impedance will not affect the total amount of current delivered to the tissue. Current controlled waveforms can ensure that the electric field in the tissue is independent of electrode polarization or the voltage drop across the electrode-electrolyte interface. Alternatively, the systems of the present disclosure can be configured or programmed to use voltage-controlled stimulation.

In some examples, the implantable medical device 30 includes or defines a connector enclosure assembly, a main enclosure assembly, electrical circuitry, and a battery. The battery is electrically coupled to the electrical circuitry and maintained in the main enclosure assembly. The connector enclosure assembly is coupled to the main enclosure assembly and, in one example, includes conductor fingers that are electrically connected to individual circuitry components, and in particular contact pads of the electrical circuitry. The electrical circuitry generates electrical signals, which are delivered to the connector enclosure assembly via the conductor fingers. The connector enclosure assembly further forms or defines an entryway sized to receive the proximal end of the implantable medical lead. Electrical connectors provided with the connector enclosure assembly interface with the electrical contacts and are electrically connected to respective ones of the conductor fingers, which connects the electrical circuitry with implantable medical lead.

The main enclosure assembly can assume various forms appropriate to maintain the electrical circuitry and the battery, as well as for assembly with the connector enclosure assembly. The electrical circuitry can include various electrical components and connections appropriate to provide, in some examples, a pulse generator for therapy stimulation, e.g., a constant current stimulation engine, sensing circuitry for measuring physiological parameters, telemetry for communication with external devices, memory, and a recharge circuit including the secondary coil. For example, the electrical circuitry can deliver stimulation signals, and can process or act upon received sensed signals. The electrical circuitry optionally provides various stimulation signal parameters, for example current controlled amplitude with a resolution of 0.1 mA steps, an upper limit of 12.5 mA, and a lower limit of 0.0 mA; a rate of 3-130 kHz; pulse width increments of 10 µs steps with a maximum of 450 µs and a minimum of 20 µs. The battery can include a rechargeable battery that assumes various forms appropriate to provide power for generating desired stimulation signals and to store power provided from the recharge circuitry. For example, the battery can incorporate lithium ion (Li+) chemistry, i.e., a lithium ion battery.

The charger 32 is available in different configurations depending on recharge frequencies and communication schemes for use with the implantable medical device 30. For example, a first configuration of the charger 32 may support a bidirectional inductive telemetry communication scheme and an 8.9 kHz recharge frequency, a second configuration of the charger 32 may support a radiofrequency telemetry and downlink inductive telemetry communication schemes and a 40 kHz recharge frequency, and a third configuration may support the bidirectional inductive telemetry communication scheme and a 110 kHz recharge frequency. Other recharge frequencies and combinations of recharge frequencies and communication schemes are contemplated.

In general, the charger 32 delivers magnetic energy to a corresponding implantable device 30 at the preselected frequency with a resonant inductor-capacitor (LC) tank circuit to generate an H-field. The tank circuit includes a recharge coil in series with a recharge capacitor. Various configurations of the charger 32 can share a common coil design, and the preselected recharge frequency is determined via a selected tank capacitance of the recharge capacitor. The tank circuit can oscillate at a resonant frequency. A phase locked loop in the tank circuit is created via pulsing an applied tank voltage in phase with a tank current. During resonance, the tank current is approximately or generally sinusoidal over time. The tank circuit can achieve maximum tank power when a tank voltage pulse is aligned in time with the tank current. Recharge power can be adjusted by altering the magnitude and duty of the tank voltage pulse input to the tank circuit.

Figure 2:
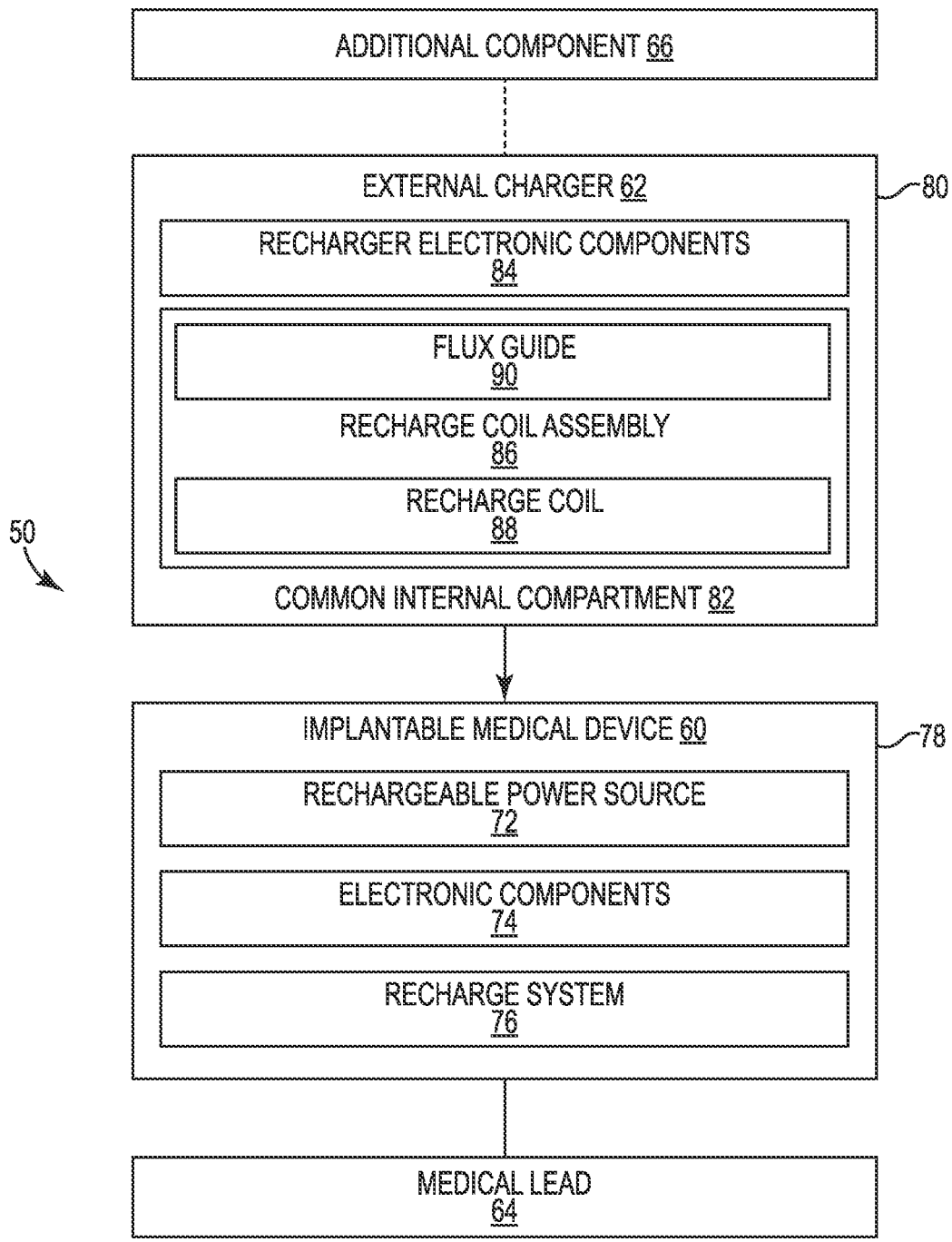
FIG. 2 is another schematic diagram illustrating an example implantable medical system including an implantable medical device configured as implantable neurostimulator and an external charger having an internal compartment with a flux guide of the present disclosure, which may be included in the example implantable medical system of FIG. 1.

FIG. 2 illustrates an implantable medical device system 50, which can correspond with system 20. The system 50 includes an example implantable medical device 60, which can correspond with implantable medical device 30, that is configured as an implantable neurostimulator. The system 50 further includes an example external charger 62, or wireless charger, which can correspond to the charger 32, to inductively transfer energy to the example implantable medical device 60. The example implantable medical device 60 is configured to use current controlled stimulation to generate an electric field to modulate the sacral nerve. Electrical stimulation is delivered using metal electrodes provided with an implantable medical lead 64 coupled to implantable medical device 60. In one example, the system 50 can include an additional component 66, such as additional components, that can include a handset programmer to wirelessly interface with the implantable medical device 60 or with the charger 62, a charging dock to charge the charger 62, or a fixation product to hold the charger 62 in place against a patient, such as patient 22.

The example implantable medical device 60 includes a rechargeable power source 72, electronic components 74 coupled to the rechargeable power source 72, and a recharge system 76 coupled to the rechargeable power source 72 within an enclosure 78. The electronic components 74 deliver a therapy to or monitor a parameter of a patient, such as via electrical stimulation. In one example, the electronic components 74 include a communication module to communicate with the charger 62 and can be configured to communicate with a handset programmer, which may be included in a mobile computing device, in additional component 66. In one example, the rechargeable power source 72 is a rechargeable battery. The recharge system 76 includes a secondary coil to receive power via an inductive power transfer from the charger 62.

The external charger 62 includes a housing 80 forming an internal compartment 82, recharger electronic components 84 disposed in the internal compartment 82, and a recharge coil assembly 86 disposed within the internal compartment 82. In one example, the recharger electronic components 84 are disposed on a printed circuit board assembly in the internal compartment 82. The recharger electronic components 84 may include or be coupled to a power source such as a rechargeable battery. The recharge coil assembly 86 includes a recharge coil 88 to provide power to the secondary coil in the recharge system 76 of the example implantable medical device 60 via the inductive power transfer. The recharge coil assembly 86 also includes a flux guide 90 having a ferrite sheet disposed between the recharge coil 88 and the printed circuit board assembly of the electronic components 84.

In one example, the recharge coil assembly 86 includes an insulative bobbin having a first major surface and an opposite second major surface, the recharge coil 88, a telemetry coil, and the flux guide 90. The recharge coil 88 is disposed on the first major surface of the insulative bobbin and coupled to the recharger electronic components 84 to form a resonant recharge tank circuit to provide power to the secondary coil of the example implantable medical device 60 via inductive power transfer. The telemetry coil can be disposed concentric to the recharge coil 88 on the first major surface of the insulative bobbin and operably coupled to the electronic components 84 to form a resonant telemetry tank circuit to provide inductive telemetry with the implantable medical device 60. The flux guide 90 having the ferrite sheet is disposed on the second major surface of the insulative bobbin and between the recharge coil 88 and telemetry coil and the main printed circuit board assembly.

Figure 3:
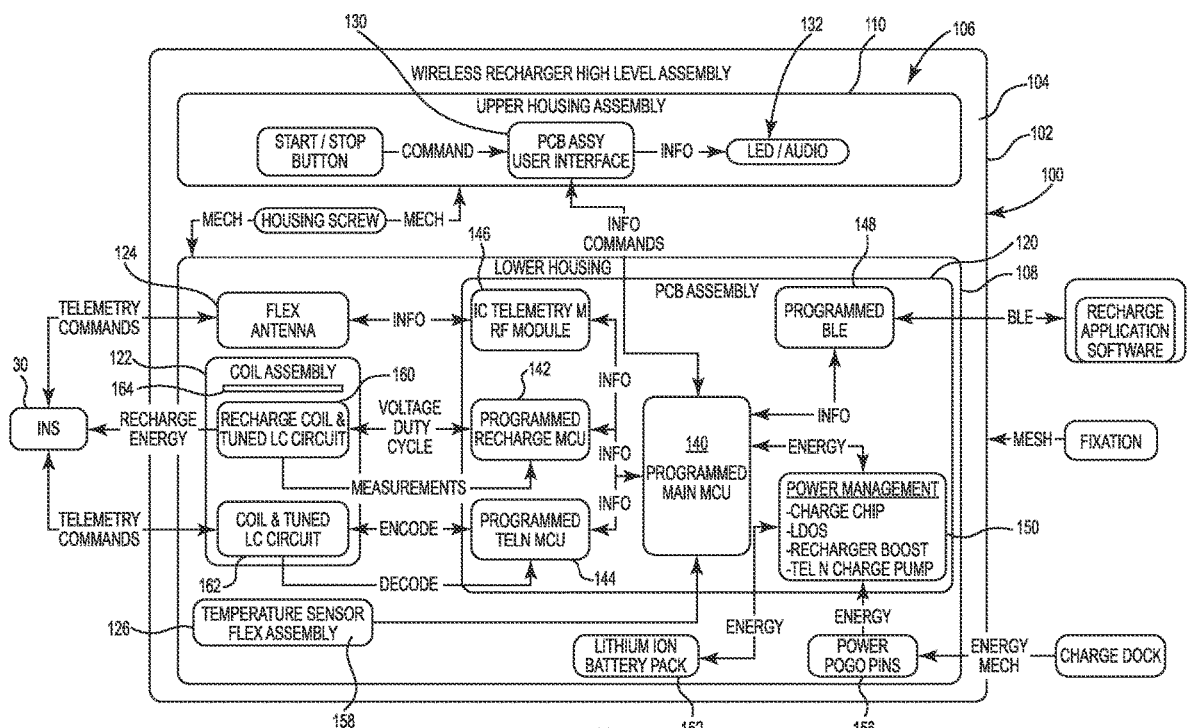
FIG. 3 is a block diagram illustrating physical components of the external charger of FIG. 1 or 2.

FIG. 3 illustrates a charger 100, which can correspond with charger 32. The charger 100 includes a housing 102 that forms a common internal compartment 104. The internal compartment 104 includes the components 106 of the charger 100. In one example, the internal compartment 104 within the housing 102 includes a first housing assembly 108 and a second housing assembly 110 with the components 106, although examples are contemplated in which components 106 are included on one or more housing assemblies within the internal compartment 104. The first housing assembly 108 can include a main printed circuit board assembly 120, a recharge coil assembly 122, a flex antenna 124, and a temperature sensor flex assembly 126. The second housing assembly 110 may include a user interface printed circuit board assembly 130 and user interface components 132.

The main printed circuit board assembly 120 includes a main microcontroller unit (MCU) 140 that can be coupled to follower microcontrollers such as programmed recharge MCU 142 and a programmed inductive telemetry MCU 144, such as a Telemetry N MCU. The main MCU 140 can also be coupled to a radiofrequency telemetry module 146, such as Telemetry M radiofrequency module if the charger supports a radiofrequency, or a Telemetry M, communication feature. The main printed circuit board assembly 120 can include an additional communication module 148, such as a Bluetooth Low Energy module, to communicate with a remote handset programmer if included with the system 20. The main printed circuit board assembly 120 also includes a power management circuit 150, which is also operably coupled to the main MCU 140. The power management circuit 150 can be coupled to a charger power source 152, such as a rechargeable lithium ion battery and to charger pins 156. In one example, charger pins 156 may interface with a charging dock to receive power to recharge the battery 152 is the charging dock is included with the system 20. The main MCU 140 can also be coupled to the temperature sensor flex assembly 124, that is strategically located in the charger 100 to provide a temperature measurement signal to the main MCU 140.

The recharge coil assembly 122 is operably coupled to the main printed circuit board assembly 120 within the internal compartment 104 and as part of the first housing assembly 108. The recharge coil assembly 122 includes a recharge coil and tuned LC circuit 160, a telemetry coil and tuned LC circuit 162, such as a coil for inductive telemetry, or Telemetry N, and a flux guide 164. The recharge coil and tuned LC circuit 160 serves as the primary coil to generate the H-field and charge the implantable medical device 30. The recharge coil and tuned LC circuit 160 is coupled to components on the main printed circuit board assembly 120 such as the programmed recharge MCU 142 to receive a voltage duty cycle signals and provide return signals to the recharge MCU 142 that can be used to moderate the voltage duty cycle signal. The telemetry coil and tuned LC circuit 162 is also coupled to components on the main printed circuit board assembly 120 such as the inductive telemetry MCU 144 to receive communication signals from the inductive telemetry MCU 144 and to transmit a Telemetry-N communication signal to the implantable medical device 30 as well as receive a communication Telemetry-N communication signal from the implantable medical device 30 and provide the signal to the inductive telemetry MCU 144.

The radiofrequency telemetry module 146 is coupled to a flex antenna 124 and configured to generate a signal to communicate commands with the implantable medical device 30, such as Telemetry-M commands that are exchanged between the radiofrequency telemetry module 146 and the implantable medical device 30.

Figure 4:
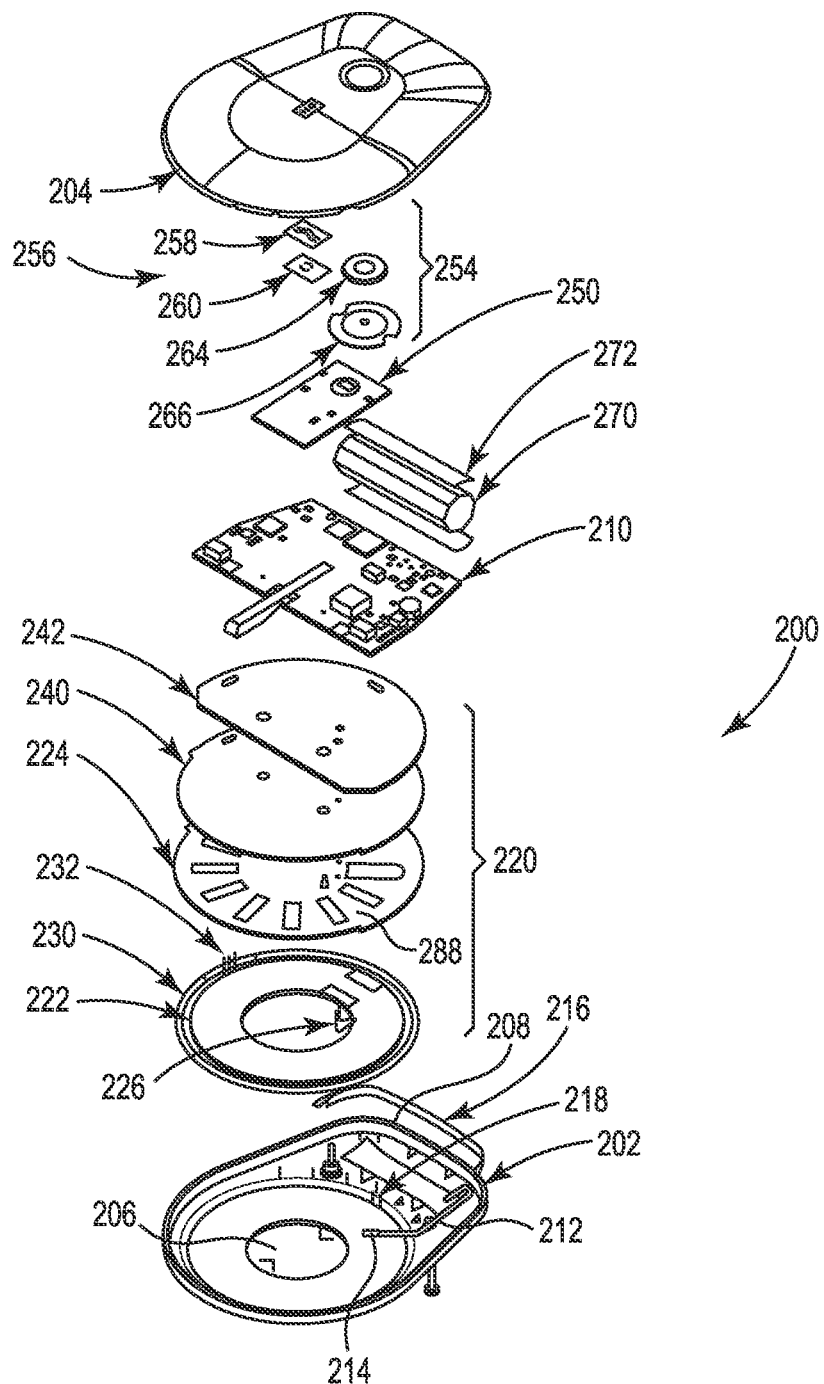
FIG. 4 is an exploded perspective view illustrating physical components of the external charger of FIG. 3.

FIG. 4 illustrates an exploded view of a charger 200, which can correspond with charger 100 and demonstrate an example of arrangement of components of the charger within the internal compartment 104. The charger 200 includes a first housing portion 202 and a second housing portion 204. The first and second housing portions 202, 204 are included in an outer shell of the of the charger 200, or housing 102, and serve to define the internal compartment 104 within the housing 102.

The first housing portion 202 includes a main wall 206 that can provide a surface to interface with a transcutaneous boundary 24. During a recharge session with the implantable medical device 30, the main wall 206 is placed against the patient 22 and over the implantable medical device 30. The first housing portion 202 can include an upstanding edge 208 that can surround the main wall 206. The main wall 206 can be configured to interface directly against the patient 22 or through a fixation product such as a fixation belt or fixation drape of the system 20.

Charger 200 further includes a main printed circuit board assembly 210, which can correspond with the main printed circuit board assembly 120 and include respective electrical components. The main printed circuit board assembly 210 can include electrical components to couple with a temperature flex assembly 212 including a temperature sensor 214 disposed against the main wall 206. Additionally, if the charger 200 includes a radiofrequency telemetry feature, such as Telemetry-M, a corresponding electrical component on the main printed circuit board assembly 210, such as the radiofrequency telemetry module 146, is coupled to a flex antenna 216, which can be attached to and upstanding along the upstanding edge 208 at a back of the first housing portion 202. If the charger does not include a feature to perform the communication via the radiofrequency telemetry feature, the corresponding electrical components may not be populated on the main printed circuit board 210 and the flex antenna 216 may not be included. In the example in which the radiofrequency telemetry feature is Telemetry M, which uses the Medical Device Radiocommunications Service (MedRadio), formerly Medical Implant Communication Service (MICS), frequency band for communication with the implantable medical device 30. The radiofrequency telemetry module can be provided in a land grid array package with a radiofrequency shield. A monopole antenna based on a λ/4 radiator at 400 MHz is 18.75 cm, but the radiofrequency telemetry flex antenna is of a shorter length due to constraints of the internal compartment.

In the example, electronic components on the main printed circuit board assembly 210, such as a power management circuit 150, can interface with a charging dock of system 20 via pogo pins 218 operably coupled to the main printed circuit board assembly and extending through the housing such as through the first housing portion 202.

The charger 200 includes a recharge coil assembly 220, which can correspond with the recharge coil assembly 122. The recharge coil assembly 220 is disposed between the main wall 206 and the main printed circuit board assembly 210. In the example, the recharge coil assembly 220 includes a generally planar flat recharge coil 222 having a concentric winding around a plastic bobbin 224. The recharge coil 222 is generally parallel to a plane generally defined by the main wall 206. The example recharge coil 222 does not include a magnetic core. Rather, the bobbin 224 can define an air core for the recharge coil 222. The recharge coil 222 serves as a primary coil in a resonant tank circuit to generate the H-field. In one example, a single wire is wrapped concentrically around the plastic bobbin 224 to form the recharge coil 222. Each end of the wire can be formed into or attached to pins 226 or receptacles that are coupled to an electrical component on the main printed circuit board assembly 210 to form the tank circuit. The plastic bobbin 224 can be formed to include an inner annular channel (not shown) to receive the recharge coil 222.

The recharge coil assembly 220 can also include a generally planar flat inductive telemetry coil 230, such as a Telemetry-N coil, to provide for inductive communication with the implantable medical device using the Telemetry-N protocol. In one example, the inductive telemetry MCU 144 can decode standard amplitude-shift keying (ASK) decoding by receiving an amplitude modulated burst with a carrier of 175 kHz through the inductive telemetry coil 230. The burst is then sent through a band pass/amplifier circuit included in the electronic components on the main printed circuit board assembly 210. From the amplifier, the signal is passed to a logarithmic amplifier circuit to form an envelope of the signal. The signal passes through a low pass filter and then to a comparator to convert the base band data into a digital signal. The signal is then sent to a microprocessor for decoding. The transmit circuit is an H-Bridge configuration that generates modulated bursts at a carrier frequency of 175 kHz and a data rate of 4.4 kbps. In the example, the inductive telemetry coil 230 is formed concentrically around and spaced apart from the recharge coil 222, such as in an outer annular channel (not shown) on the plastic bobbin 224 spaced apart from the inner annular channel. In one example, a single wire is wrapped concentrically around the plastic bobbin 224 to form the inductive telemetry coil 230. Each end of the wire can be attached to or formed into pins 232 or receptacles that are coupled to an electrical component on the main printed circuit board assembly 210, such as an H-bridge in the inductive telemetry MCU 144.

The recharge coil assembly 220 includes a planar flux guide 240 disposed alongside the planar recharge coil 222 and between the recharge coil 222 and the main printed circuit board assembly 210. The flux guide 240 includes a ferrite shield to concentrate magnetic flux and reduce the height of a H-field generated on the side of the main printed circuit board assembly 210, or opposite the recharge coil 222. The inclusion of the flux guide 240 results in more flux as measured in Webers (Wb) for a given electrical current through the recharge coil 222 than without the flux guide 240, and increases the total inductance of the recharge coil 222. The flux guide 240 further reduces losses in the recharge coil 222 as a result of, for example, conductivity in the ground plane of the circuit board assemblies 210, which is discussed below. A flux guide 240 is of a size to cover both the recharge coil 222 and the first telemetry coil 230 and can be circular, or generally circular in shape. In one example, the flux guide 240 is constructed from three ferrite sheets of approximately 0.3 mm thick each adhered together to form a single flux guide sheet of approximately 1 mm thick. Each ferrite sheet can be constructed from porous NiCuZn Ferrite that may include a 3 mm square grid pattern of score lines to provide some flexibility in the ferrite sheet.

In the example, a foam padding 242 is disposed between the recharge coil assembly 220 and the main printed circuit board assembly 210. The foam padding 242 can be a flat sheet of foam that includes a silhouette formed to the shape of the recharge coil assembly 220. The foam padding 242 can be included to space the recharge coil assembly 220 from the main printed circuit board assembly 210, urge the recharge coil assembly against the main wall, or to protect the components in the internal compartment of the housing from shock.

A second printed circuit board assembly 250, such as a user interface printed circuit board assembly, can be disposed between the main printed circuit board assembly 210 and the second housing portion 204. The second printed circuit board assembly can support user interface elements 254 and be operably coupled to the main printed circuit board assembly. User interface elements 254 can include lights, buttons, displays, or other features to receive user inputs or provide information to the user of the charger 200. For example, user interface elements 254 include a light 256 having components including a light pipe 258 and shelter 260 and a power button 262 having components including a power button actuator 264 and a seal 266. The light 256 and power button 262 can be coupled to electronic components on the second printed circuit board assembly 250.

An internal battery 270 can be disposed against or proximate the back of the first and second housing portions 202, 204, such as proximate the second telemetry flex antenna 216. The internal battery can be disposed alongside the main printed circuit board assembly 210 and the recharge coil assembly 220. In the example, a foam padding 272 is coupled to the battery 270. The battery 270 can be operably coupled to electronic components on the main printed circuit board assembly 210, such as a power management circuit 150.

A ground plane on a printed circuit board is generally a large area or layer of a conductive foil such as copper foil connected to the ground, which may include a terminal of the power supply. The ground plane serves as the return path for current from many different components. Typically, the ground plane is made as large as possible, covering most of the area of the printed circuit board which is not occupied by circuit traces. In multilayer circuit boards, the ground plane is often a separate layer covering the entire circuit board.

This serves to make circuit layout easier, allowing the designer to ground any component without having to run additional traces. Electronic component leads that are to be grounded are routed directly through a hole in the board to the ground plane on another layer. The large area of the foil also conducts the large return currents from many components without significant voltage drops, which permits for a consistent reference potential. The ground plane, however, contributes to loading the primary coil and to generating reflected impedance in the primary coil that are significant.

In one example, the configuration or distribution of the electronic components on the main printed circuit board assembly 210 can be selected to reduce the reflected impedance. For example, the circuit board of the main printed circuit board assembly 210 can be selected to be generally annular and in the shape of the recharge coil to fit over the recharge coil assembly 220. In another example, or in addition a selected shape of the main printed circuit board assembly 210, the ground plane can be manufactured to include various cut outs or slits of different sizes, lengths, or configurations to reduce reflected impedance. In still a third configuration, multiple, layered printed circuit board assemblies, such as the second printed circuit board assembly 250 disposed above the main printed circuit board assembly 210 within the internal compartment can reduce reflected impedance.

Figure 5:
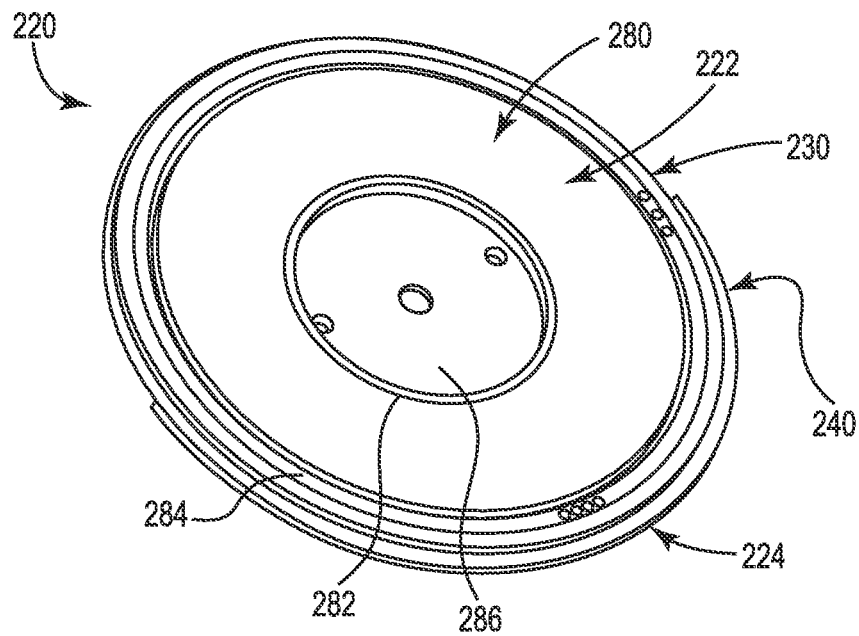
FIG. 5 is a perspective view illustrating an example recharge coil assembly of the external charger of FIG. 3.
Figure 6:
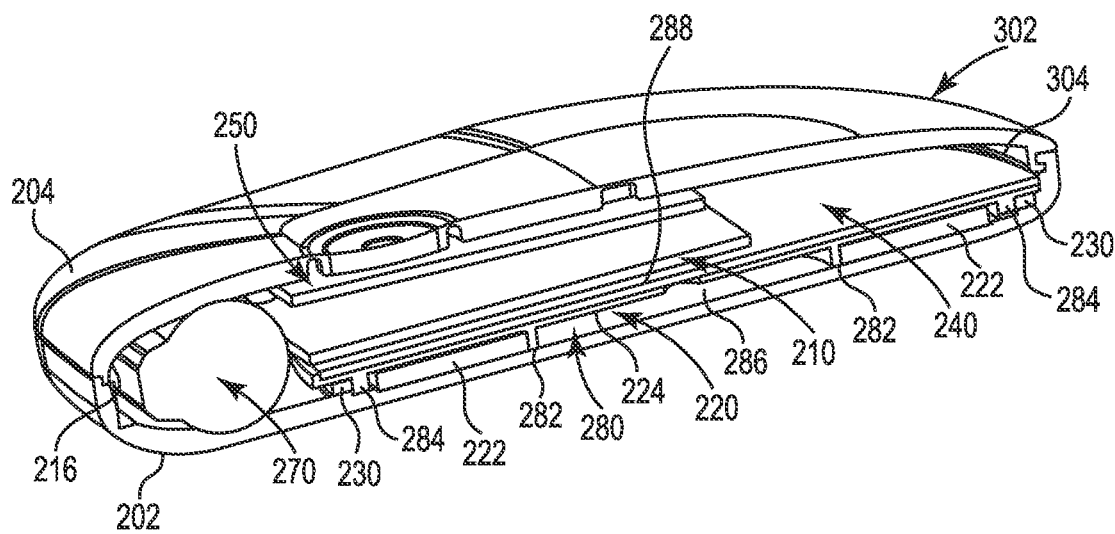
FIG. 6 is a perspective cross section view illustrating physical components including a recharge coil assembly of the external charger of FIG. 3.

FIG. 5 illustrates the recharge coil assembly 220 as viewed from a first major exterior 280, which interfaces with the main wall 206 of the first housing portion 202 in the assembled charger 200. The recharge coil assembly 220 in the example includes the plastic bobbin 224, the recharge coil 222, the inductive telemetry coil 230, and the planar flux guide 240.

The example recharge coil assembly 220 includes the plastic bobbin 224 having a generally circular internal ridge 282 and a generally circular external ridge 284 on first major surface 286 forming a generally circular internal annular channel having a generally flat surface between the internal ridge 282 and the external ridge 284. Additionally, the plastic bobbin 224 can include a generally circular external annular channel having a generally flat surface outside of the external ridge 282. In one example, the generally flat surface of the external annular channel is in the plane of the generally flat surface of the internal annular channel on the first major surface 286.

The flat recharge coil 222 is disposed into the internal annular channel between the internal ridge 282 and the external ridge 284. The recharge coil assembly 220 does not include a core, such as magnetic core within the internal ridge 282, and the recharge coil 222 is coreless. In one example, the recharge coil 222 is formed from 127 turns of twenty-five strand, thirty-eight American Wire Gauge (AWG) litz wire, and includes an inner diameter of about 45 mm, an outer diameter of about 91 mm, and a depth of about 3 mm. In one example, the recharge coil 222 in the assembled recharge coil assembly includes an inductance of approximately 2.05 mH.

The recharge coil assembly 220 can be included in various models or configurations of the charger 200 to deliver magnetic energy at a preselected frequency. For example, a charger can deliver magnetic energy to the implanted medical device 30 at one of 9 kHz, 40 kHz, and 110 kHz. The recharge frequency can be determined by selecting an appropriate tank capacitor. A tank capacitor in series with the recharge coil 222 having an inductance L for the primary coil tank circuit can include a tuning or tank capacitance C based from the selected resonant frequency f as $$C = 1/L \cdot (2\pi f)^2$$

The recharge coil 222 is configured to deliver magnetic energy at a recharge frequency over a range of recharge frequencies based on a tank capacitor having a selected tank capacitance over a range of tank capacitances. In one example, the selected tank capacitor can be included on the main printed circuit board assembly 210, and included in the same location on the main printed circuit board assembly 210 so as to be populated during manufacturing. During manufacturing, a selected main printed circuit board assembly with a particular capacitance value for the tank capacitor can be coupled to the recharge coil 222, or recharge coil assembly 220, to provide the selected recharge frequency. This permits the use of a single design and configuration of the recharge coil assembly 220 to be used for multiple models of chargers 200 for use with different recharge frequencies.

The flat inductive telemetry coil 230 is disposed into the external annular channel external to external ridge 284. The recharge coil assembly 220 does not include a core, such as magnetic core within the internal ridge 282 or otherwise, and the inductive telemetry coil 230 is coreless. In one example, the inductive telemetry coil 230 is formed from twenty-five turns of thirty American Wire Gauge (AWG) litz wire, and includes an inner diameter that is greater than the outer diameter of the recharge coil 222. At 175 kHz, a free space antenna inductance is 211 µH and a resistance is 5Ω. In one example, the charger 200 can use the inductive telemetry coil 230 to both send and receive communication. A receiver bandpass filter can be tuned to greater than 175 kHz to avoid environmental noise such as radio-frequency identification (RFID). In one example, the tuning capacitor of the inductive telemetry tank circuit can be 3300 pF.

The recharge coil 222 and inductive telemetry coil 230, being concentric and proximate each other, have a relatively strong mutual magnetic coupling. An active one of the recharge coil 222 and the inductive telemetry coil 230 can produce sympathetic current in an inactive one of the recharge coil 222 and the inductive telemetry coil 230. The sympathetic current in the inactive coil is undesirable in that it wastes energy in coil resistance and the sympathetic current can cancel a portion of the desired H-field of the active coil. To remove coil interaction effects, electronic components include relays to open the respective tank circuit of the inactive coil. Capacitors for the recharge and inductive telemetry tank circuits can be selected to account for stray capacitance from the relays.

The flux guide 240 is coupled to a second major surface 288 (indicated in FIG. 3) of the plastic bobbin 224. The second major surface 288 is opposite the first major surface 286, and the recharge coil 222 and inductive telemetry coil 230 are spaced apart and electrically insulated from the flux guide 240. The flux guide 240 is sized and shaped to cover the recharge coil 222 and inductive telemetry coil 230. In one example, the flux guide 240 is sized and shaped to be opposite the internal annual channel and the external annular channel of the plastic bobbin 224. In the illustrated example, the flux guide 240 covers the second major surface 288 of the plastic bobbin 224.

FIG. 5 illustrates an example of the assembled charger 200. The first housing portion 202 and second housing portion 204 are attached together to form a housing 302 having an internal compartment 304, which includes the components of the charger 200. The first major exterior 280 of the recharge coil assembly 220 interfaces with the main wall 206 of the first housing portion 202. In the example, the internal ridge 282 and external ridge 284 of the first major surface 286 of the plastic bobbin 224 are urged against the main wall 206. The recharge coil 222 and inductive telemetry coil 230 are coupled to the first major surface 286 in the respective annular channels to interface with the main wall 206. The flux guide 240 is disposed on the second major surface 288 of the recharge coil assembly 220 and extends over the recharge coil 222 and the inductive telemetry coil 230 opposite the first major surface 286. The main printed circuit board assembly 210 and the second interface printed circuit board assembly 250 are included in the internal compartment 304 between the recharge coil assembly 220 and the second housing portion 204. The battery 270 is included adjacent the recharge coil assembly 220 and the main and second printed circuit board assemblies 210, 250. In the example, the flex antenna 216 is disposed against the housing 302 proximate the battery 270.

During a recharge session, the charger 200 can be placed against a patient at a transcutaneous boundary such that an axis extending generally perpendicular to the first major surface of 286 of the plastic bobbin 224 and within the internal ridge 282 extends through the implantable medical device 30.

The external charger can be constructed by selecting a recharge coil assembly comprising a flat recharge coil having a selected inductance and coupling a recharge capacitor to the flat recharge coil to form a recharge tank circuit. The recharge capacitor includes a capacitance selected from one of a plurality of capacitances, such as three capacitances, configured to be coupled to the flat recharge coil to provide the recharge tank circuit with a resonant frequency based on the selected recharge capacitor. The recharge capacitor can be coupled to a main printed circuit board assembly. A flux guide having a ferrite sheet is disposed between the recharge coil and the printed circuit board assembly. The recharge coil assembly and the main printed circuit board assembly are assembled together within a common internal compartment of a housing.

All patents referenced in the disclosure are incorporated by reference in their entireties into this disclosure.

Although the present disclosure has been described with reference to preferred embodiments, workers skilled in the art will recognize that changes can be made in form and detail without departing from the spirit and scope of the present disclosure.

What is claimed is:

1. An implantable medical system comprising:
   an implantable medical device comprising:
      electronic components to deliver a therapy to or monitor a parameter of a patient, the electronic components coupled to a rechargeable power source; and
      a recharge system operably coupled to the rechargeable power source, the recharge system including a secondary coil to receive power via an inductive power transfer; and
   an external charger comprising:
      a housing forming an internal compartment;
      recharger electronic components disposed on a printed circuit board assembly in the internal compartment; and
      a recharge coil assembly disposed within the internal compartment, the recharge coil assembly including:
         a plastic bobbin;
         a recharge coil configured to output power to the secondary coil via the inductive power transfer, wherein the recharge coil is planar and wound around the plastic bobbin; and
         a planar flux guide having a planar ferrite sheet, the ferrite sheet located between the recharge coil and the printed circuit board assembly and the ferrite sheet is disposed alongside the recharge coil and the plastic bobbin.

2. The system of claim 1 wherein the recharge coil assembly includes a telemetry coil, separate from the recharge coil, operably coupled to the recharger electronic components, the telemetry coil configured to communicate with the implantable medical device via inductive telemetry.

3. The system of claim 2 wherein the plastic bobbin defines an air core for the recharge coil and the telemetry coil.

4. The system of claim 3:
   wherein the recharge coil and the telemetry coil are both planar, flat, concentric, having a common center, co-axial, having a common axis and coplanar, in the same plane, and
   wherein the planar flux guide is configured to cover both the telemetry coil and the recharge coil.

5. The system of claim 4 wherein the recharge coil and the telemetry coil are disposed on the plastic bobbin.

6. The system of claim 4 wherein the recharge coil and the telemetry coil are generally parallel with a major wall of the housing, wherein the major wall of the housing interfaces with the patient.

7. The system of claim 6 wherein the recharge coil assembly is in contact with the major wall of the housing.

8. The system of claim 2 wherein the recharger electronic components include a telemetry capacitor coupled to the telemetry coil to form a telemetry tank circuit.

9. The system of claim 8 wherein the telemetry tank circuit includes a resonant frequency of about 175 KHz.

10. The system of claim 8 wherein the recharger electronic components include a recharge capacitor coupled to the recharge coil to form a recharge tank circuit.

11. The system of claim 10 wherein the recharge tank circuit includes a resonant frequency selected from one of about 8.9 kHz, 40 kHz, and 110 kHz.

12. The system of claim 11 wherein the recharger electronic components include relays coupled to the telemetry tank circuit and the recharge tank circuit such that if one of the telemetry tank circuit and the recharge tank circuit is active, the other of the telemetry tank circuit and the recharge tank circuit is inactive and open.

13. The system of claim 1 wherein the implantable medical device comprises an implantable neurostimulator.

14. The system of claim 13 wherein the implantable neurostimulator is coupled to an implantable medical lead.

15. The system of claim 1 wherein the external charger is disposed within a fixation product.

16. The system of claim 15 wherein the fixation product comprises one of a fixation belt or a fixation drape.

17. The system of 1 wherein the electronic components include a communication module configured to communicate with a handset programmer included in a mobile computing device.

18. The system of claim 1 wherein the external charger includes a rechargeable battery disposed in the internal compartment of the housing, wherein the recharger electronic components include a power management circuit and the rechargeable battery is coupled to a power management circuit.

19. The system of claim 18 including a charging dock operably couplable to the power management circuit via a mechanical connection.

20. The system of claim 1 wherein the implantable medical device comprises a rechargeable battery.

21. An external charger for an implantable medical device, the implantable medical device having a secondary coil in a patient, the external charger comprising:
a housing forming an internal compartment;
electronic components disposed on a printed circuit board assembly disposed within the internal compartment; and
a recharge coil assembly disposed within the internal compartment, the recharge coil assembly including:
a recharge coil configured to output power to the secondary coil via inductive power transfer wherein the recharge coil is planar; and
a planar flux guide having a planar flexible ferrite sheet, the ferrite sheet located between the recharge coil and the printed circuit board assembly and the ferrite sheet is disposed alongside the recharge coil.

22. The external charger of claim 21, wherein the recharge coil assembly includes a telemetry coil, separate from the recharge coil, operably coupled to the electronic components, the telemetry coil configured to communicate with the implantable medical device via inductive telemetry.

23. The external charger of claim 22 wherein the recharge coil and the telemetry coil comprise an air core.

24. The external charger of claim 23 wherein the recharge coil and the telemetry coil are both planar, flat, concentric, having a common center, co-axial, having a common axis and coplanar, in the same plane, and wherein the planar flux guide is configured to cover both the telemetry coil and the recharge coil.

25. The external charger of claim 24 wherein the recharge coil assembly includes an insulative bobbin, and the recharge coil and the telemetry coil are disposed on the insulative bobbin.

26. The external charger of claim 25 wherein the insulative bobbin is a plastic bobbin.

27. The external charger of claim 24 wherein the recharge coil and the telemetry coil are generally parallel with a major wall of the housing, wherein the major wall of the housing interfaces with the patient.

28. The external charger of claim 27 wherein the recharge coil assembly is in contact with the major wall of the housing.

29. The external charger of claim 22 wherein the electronic components include a telemetry capacitor coupled to the telemetry coil to form a telemetry tank circuit.

30. The external charger of claim 29 wherein the telemetry tank circuit includes a resonant frequency of about 175 KHz.

31. The external charger of claim 29 wherein the electronic components include a recharge capacitor coupled to the recharge coil to form a recharge tank circuit.

32. The external charger of claim 31 wherein the recharge tank circuit includes a resonant frequency selected from one of about 8.9 kHz, 40 kHz, or 110 kHz.

33. The external charger of claim 32 wherein the electronic components include relays coupled to the telemetry tank circuit and the recharge tank circuit such that if one of the telemetry tank circuit and the recharge tank circuit is active, the other of the telemetry tank circuit and the recharge tank circuit is inactive and open.

34. The external charger of claim 21 wherein the electronic components are configured to communicate with the implantable medical device via all of: Telemetry N, Telemetry M, Medical Device Radiocommunications Service (MedRadio), Medical Implant Communication Service (MICS), and Bluetooth Low Energy.

35. The external charger of claim 34 comprising a flex antenna disposed within the internal compartment and operably coupled to the radiofrequency telemetry module.

36. The external charger of claim 22 including a temperature sensor disposed within the internal compartment and operably coupled to the electronic components.

37. The external charger of claim 21 wherein the electronic components include a microcontroller unit.

38. The external charger of claim 37 wherein the electronic components include a power management circuit operably coupled to a rechargeable battery.

39. The external charger of claim 22 including a second printed circuit board assembly disposed in the internal compartment and operably coupled to the printed circuit board assembly, wherein the printed circuit board assembly is disposed between the flux guide and the second printed circuit board assembly.

40. An external charger for an implantable medical device having a secondary coil in a patient, the external charger comprising:
a housing forming an internal compartment;
electronic components disposed on a main printed circuit board assembly disposed within the internal compartment; and
a recharge coil assembly disposed within the internal compartment, the recharge coil assembly including:
an insulative bobbin having a first major surface and an opposite second major surface;
a recharge coil disposed on the first major surface of the insulative bobbin and coupled to the electronic components to form a resonant recharge tank circuit, the recharge coil configured to output power to the secondary coil via inductive power transfer, wherein the recharge coil is planar and wound around the insulative bobbin;
a telemetry coil disposed concentric to the recharge coil on the first major surface of the insulative bobbin and operably coupled to the electronic components to form a resonant telemetry tank circuit configured to communicate with the implantable medical device via inductive telemetry; and
a planar flux guide having a planar ferrite sheet disposed on the second major surface of the insulative bobbin and between the recharge and telemetry coils and the main printed circuit board assembly and the ferrite sheet is disposed alongside the recharge coil and the insulative bobbin.

41. The external charger of claim 40 including a second printed circuit board disposed in the internal compartment and operably coupled to the main printed circuit board, wherein the flux guide is disposed between the second printed circuit board and the recharge and telemetry coils.

42. The external charger of claim 41 wherein the second printed circuit board includes user interface components operably coupled to the electronic components.

43. The external charger of claim 41 including a rechargeable battery adjacent to the main printed circuit board, the second printed circuit board, and the recharge coil assembly.

44. The external charger of claim 43 including a flex antenna operably coupled to the electronic components to communicate via radiofrequency telemetry, the flex antenna disposed in the internal compartment between the housing and the rechargeable battery.

45. The external charger of claim 43 wherein the recharge coil and the telemetry coil are generally flat, generally concentric and generally coplanar on the first major surface of the insulative bobbin.

46. The external charger of claim 44 wherein the housing includes a main wall configured to interface with the patient, wherein the first major surface of the insulative bobbin is disposed against the main wall.

\* \* \* \* \*